(12) United States Patent
Saw et al.

(10) Patent No.: US 11,523,835 B2
(45) Date of Patent: *Dec. 13, 2022

(54) ARTHROSCOPIC DRILL BLADE AND ARTHROSCOPIC DRILL ACCESS SYSTEM MADE THEREFROM

(71) Applicant: KLSMC INSTRUMENTS, LLC, Kuala Lumpur (MY)

(72) Inventors: Khay Yong Saw, Kuala Lumpur (MY); Nathan C. Maier, Fort Myers, FL (US); Sureshan Sivananthan, Sausalito, CA (US)

(73) Assignee: KLSMC Instruments, LLC, Palo Alto, CA (US)

( * ) Notice: Subject to any disclaimer, the term of this patent is extended or adjusted under 35 U.S.C. 154(b) by 132 days.

This patent is subject to a terminal disclaimer.

(21) Appl. No.: 16/921,777

(22) Filed: Jul. 6, 2020

(65) Prior Publication Data

US 2020/0330108 A1    Oct. 22, 2020

Related U.S. Application Data

(63) Continuation of application No. 15/716,156, filed on Sep. 26, 2017, now Pat. No. 10,702,289.
(Continued)

(51) Int. Cl.
*A61B 17/16*    (2006.01)

(52) U.S. Cl.
CPC ...... *A61B 17/1675* (2013.01); *A61B 17/1615* (2013.01); *A61B 17/1631* (2013.01)

(58) Field of Classification Search
CPC . A61B 17/16; A61B 17/1604; A61B 17/1613; A61B 17/1615; A61B 17/1617;
(Continued)

(56) References Cited

U.S. PATENT DOCUMENTS 6,692,502 B1 * 2/2004 Ertl .................... A61B 17/8866
606/86 R
8,377,432 B2    2/2013 Saw
(Continued)

FOREIGN PATENT DOCUMENTS

WO    2014107729 A2    7/2014

OTHER PUBLICATIONS

Extended European Search Report for Application No. 17854136.3, dated Mar. 17, 2020.
(Continued)

*Primary Examiner* — Eric S Gibson
(74) *Attorney, Agent, or Firm* — Dorsey & Whitney LLP

(57) ABSTRACT

An arthroscopic drill for insertion into a human joint of a human body comprising an elongate body extending between a proximal end which, during use, remains external to the human body and a distal end which, when in an operative configuration, is positioned in the human joint adjacent to a target structure within the human body (e.g. preferably a joint surface); a drill bit having a proximal portion adjacent the distal end of the elongated body, the drill bit having a distal portion extending to the target structure; and an introducer sheath having a lumen with an inner diameter of at least 2 mm and a bending stiffness of approximately 0.08 Nm², wherein the operative configuration, the elongate body extends through the introducer sheath.

21 Claims, 10 Drawing Sheets

Related U.S. Application Data

(60) Provisional application No. 62/399,892, filed on Sep. 26, 2016.

(58) Field of Classification Search
CPC .............. A61B 17/162; A61B 17/1631; A61B 17/1633; A61B 17/1655; A61B 17/1657; A61B 17/1662; A61B 17/1675
See application file for complete search history.

(56) References Cited

U.S. PATENT DOCUMENTS

| | | | | |
|---|---|---|---|---|
| 8,821,494 | B2 * | 9/2014 | Pilgeram | A61B 17/0482 |
| | | | | 606/80 |
| 9,211,126 | B2 * | 12/2015 | Sikora | A61B 17/17 |
| 9,510,840 | B2 * | 12/2016 | Sikora | A61B 17/1604 |
| 9,572,587 | B2 * | 2/2017 | Sikora | A61B 17/17 |
| 9,848,894 | B2 * | 12/2017 | Burley | A61B 17/1633 |
| 9,918,721 | B2 * | 3/2018 | Sikora | A61B 17/17 |
| 10,022,131 | B1 * | 7/2018 | Burley | A61B 17/1631 |
| 10,039,554 | B2 * | 8/2018 | Sikora | A61B 17/17 |
| 10,702,289 | B2 * | 7/2020 | Saw | A61B 17/1675 |
| 2004/0147932 | A1 * | 7/2004 | Burkinshaw | A61B 17/1675 |
| | | | | 606/79 |
| 2005/0033292 | A1 | 2/2005 | Teitelbaum et al. | |
| 2005/0177168 | A1 * | 8/2005 | Brunnett | A61B 17/1624 |
| | | | | 606/80 |
| 2005/0261684 | A1 | 11/2005 | Shaolian et al. | |
| 2008/0249481 | A1 * | 10/2008 | Crainich | A61B 17/8805 |
| | | | | 606/80 |
| 2010/0082033 | A1 * | 4/2010 | Germain | A61B 17/1604 |
| | | | | 606/86 R |
| 2010/0191248 | A1 | 7/2010 | Mehta et al. | |
| 2010/0249786 | A1 * | 9/2010 | Schmieding | A61B 17/1675 |
| | | | | 606/80 |
| 2011/0015674 | A1 * | 1/2011 | Howard | A61B 17/1739 |
| | | | | 606/232 |
| 2011/0015675 | A1 * | 1/2011 | Howard | A61B 17/1739 |
| | | | | 606/232 |
| 2011/0208194 | A1 * | 8/2011 | Steiner | A61B 17/1764 |
| | | | | 606/80 |
| 2011/0251615 | A1 * | 10/2011 | Truckai | A61B 17/1633 |
| | | | | 606/191 |
| 2011/0295262 | A1 * | 12/2011 | Germain | A61B 17/1671 |
| | | | | 606/84 |
| 2012/0071876 | A1 * | 3/2012 | Stoll | A61B 17/1631 |
| | | | | 606/96 |
| 2013/0197644 | A1 * | 8/2013 | Cloutier | A61B 17/1671 |
| | | | | 606/279 |
| 2013/0296864 | A1 * | 11/2013 | Burley | A61B 17/1631 |
| | | | | 606/80 |
| 2013/0317506 | A1 * | 11/2013 | Sikora | A61B 17/17 |
| | | | | 606/80 |
| 2014/0031825 | A1 * | 1/2014 | Torrie | A61B 17/1664 |
| | | | | 606/79 |
| 2015/0342619 | A1 * | 12/2015 | Weitzman | B65H 81/06 |
| | | | | 242/430 |
| 2016/0022279 | A1 * | 1/2016 | Sikora | A61B 17/1604 |
| | | | | 606/79 |
| 2016/0022280 | A1 * | 1/2016 | Sikora | A61B 17/17 |
| | | | | 606/80 |
| 2017/0281311 | A1 * | 10/2017 | Aloise | A61B 17/1617 |
| 2017/0303934 | A1 * | 10/2017 | Sikora | A61B 17/1675 |
| 2017/0333052 | A1 * | 11/2017 | Ding | A61B 17/00234 |
| 2017/0354423 | A1 * | 12/2017 | Piccirillo | A61B 17/1631 |
| 2018/0008285 | A1 * | 1/2018 | Sikora | A61B 17/17 |
| 2018/0065235 | A1 * | 3/2018 | Krause | B23B 45/005 |
| 2018/0084985 | A1 * | 3/2018 | Saw | A61B 17/1675 |
| 2018/0258979 | A1 * | 9/2018 | Omohundro | F16C 1/08 |
| 2018/0271542 | A1 * | 9/2018 | Sikora | A61B 17/17 |
| 2019/0069908 | A1 * | 3/2019 | Zilberman | A61B 17/1631 |
| 2019/0201007 | A1 * | 7/2019 | Sikora | A61B 17/1675 |
| 2020/0330108 | A1 * | 10/2020 | Saw | A61B 17/1615 |

OTHER PUBLICATIONS

International Search Report and Written Opinion received for PCT Appl. PCT/US2017/053506 dated Nov. 20, 2017.

Saw, Khay-Yong et al., "Articular Cartilage Regeneration With Autologous Peripheral Blood Progenitor Cells and Hyaluronic Acid After Arthroscopic Subchondral Drilling: A Report of 5 Cases With Histology", Arthroscopy: The Journal of Arthroscopic and Related Surgery, vol. 27, No. 4 Apr. 2011: pp. 493-506.

Saw, Khay-Yong et al., "Articular Cartilage Regeneration With Autologous Peripheral Blood Stem Cells Versus Hyaluronic Acid: A Randomized Controlled Trial", Arthroscopy: The Journal of Arthroscopic and Related Surgery, vol. 29, No. 4 Apr. 2013: pp. 684-694.

* cited by examiner

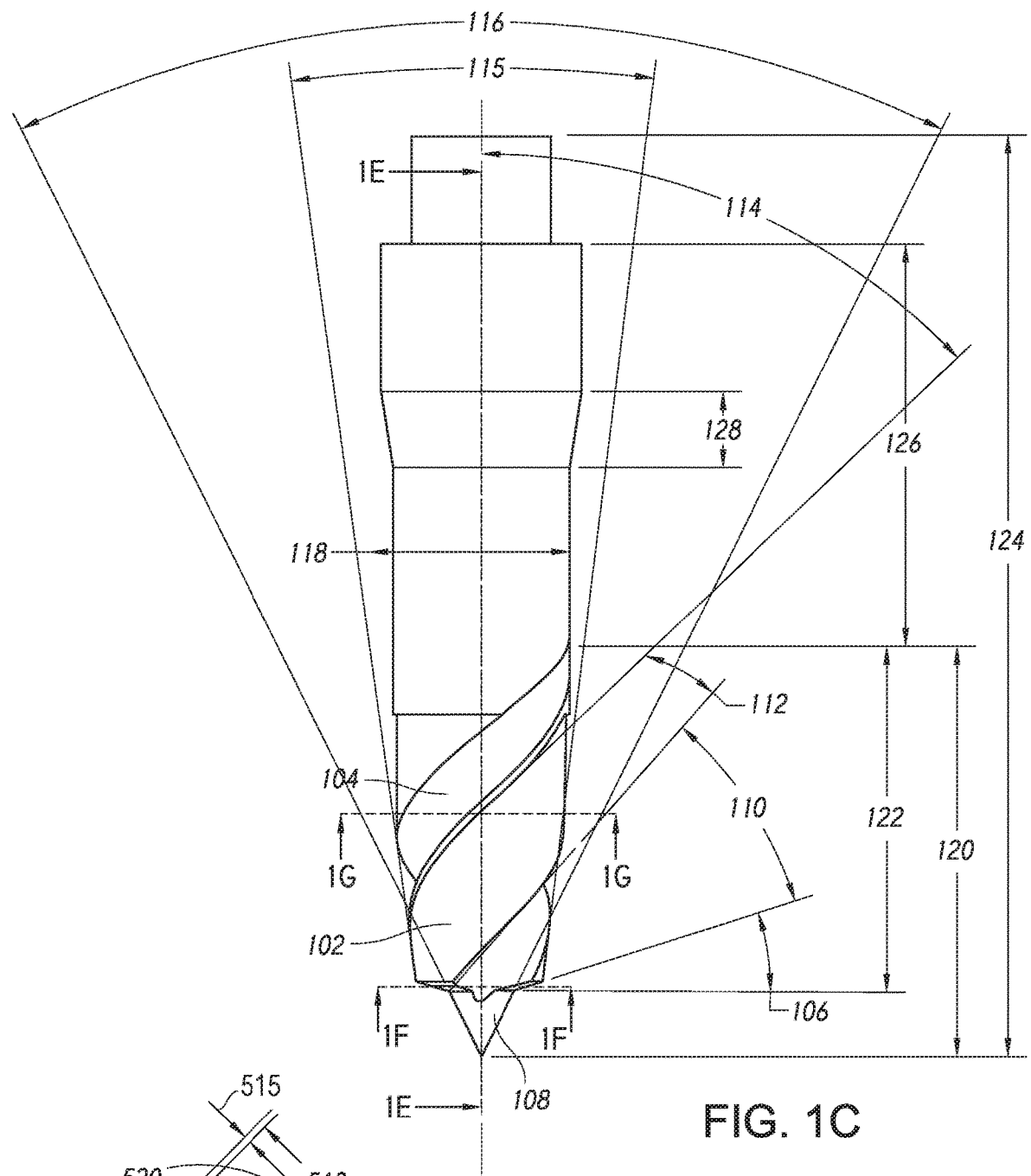
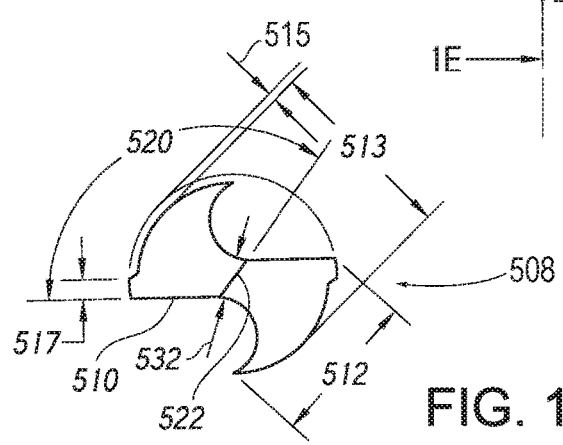
FIG. 1C
FIG. 1D

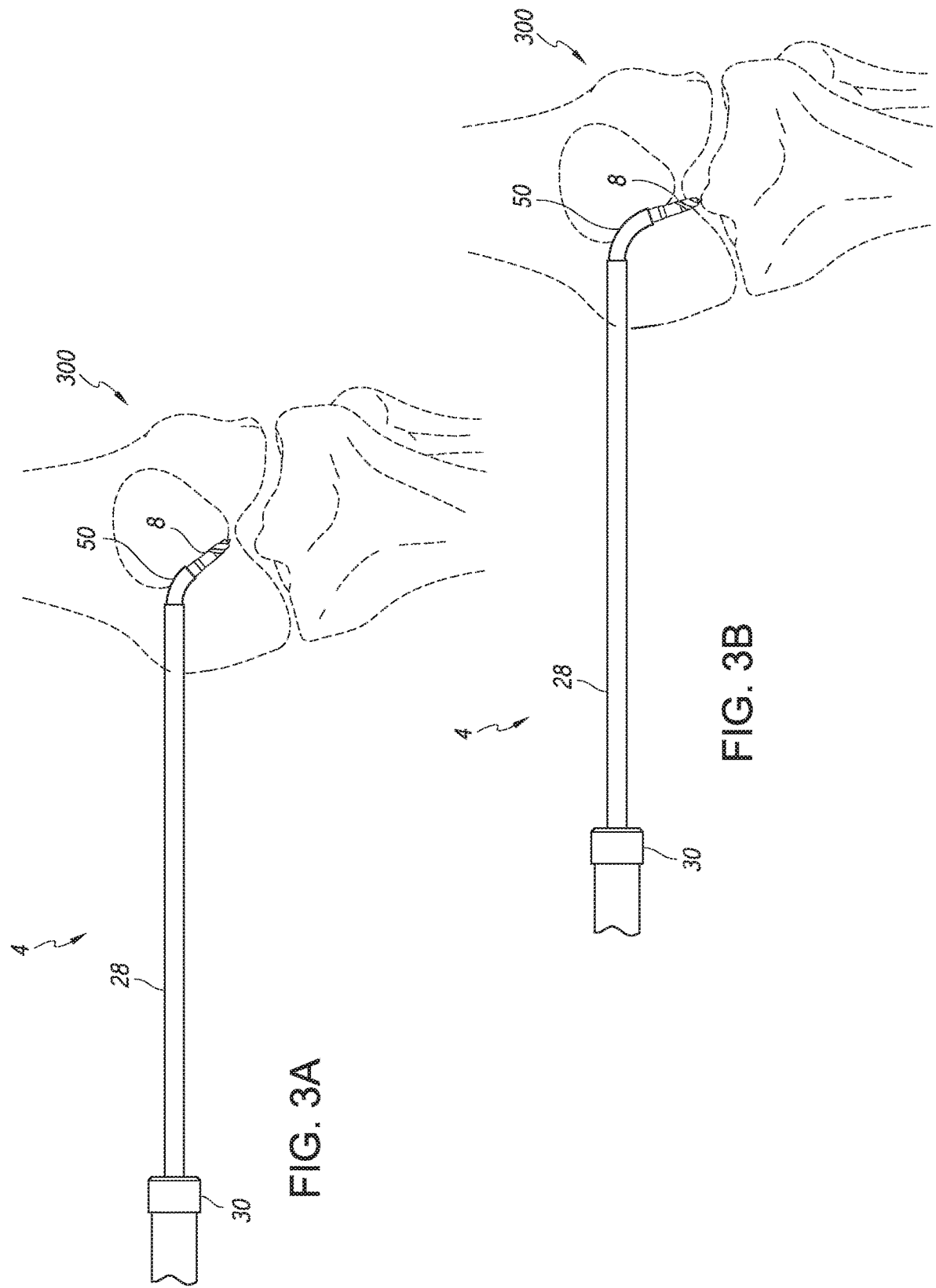

US 11,523,835 B2

ARTHROSCOPIC DRILL BLADE AND ARTHROSCOPIC DRILL ACCESS SYSTEM MADE THEREFROM

CROSS-REFERENCE TO RELATED APPLICATION(S)

This application is a continuation of U.S. application Ser. No. 15/716,156 filed Sep. 26, 2017, issued as U.S. Pat. No. 10,702,289 on Jul. 7, 2020, which claims priority to U.S. Provisional Application No. 62/399,892, filed Sep. 26, 2016, which are incorporated herein by reference, in their entirety, for any purpose.

TECHNICAL FIELD

Examples described herein relate generally to interchangeable blade systems for arthroscopic drilling. Examples of arthroscopic suction drilling and shaving systems are described and, in some embodiments, steerable drilling and shaving systems are described combining an arthroscopic drill blade with optional suction drilling for access to the joint space without utilization of open surgical procedures.

BACKGROUND

Due to increasing popularity of arthroscopic surgical procedures, a significant number of specific surgical instruments have been developed. The standard arthroscopic burr or drill driver has become increasingly useful for drilling, shaving, and generally making revisions in joint pockets with limited space available.

Currently, many surgeons are using arthroscopic suction burr driver handpiece systems such as the Stryker Formula Shaver handpiece or the Smith & Nephew DYONICS Powermax Elite to drill and shave as the arthroscopic drills of choice.

Moreover, situations may arise when it may be desirable for the surgeon to steer the active working end of the blade to multiple locations inside the joint during joint arthroscopy (including in areas where the opposite joint surface acts as an overhang which obstructs access).

SUMMARY

In an example of an arthroscopic drill for insertion into a human joint of a human body, the arthroscopic drill comprises an elongate body extending between a proximal end which, during use, remains external to the human body and a distal end which, when in an operative configuration, is positioned in the human joint adjacent to a target structure within the human body (e.g. preferably a joint surface); a drill bit having a proximal portion adjacent the distal end of the elongated body, the drill bit having a distal portion extending to the target structure; and an introducer sheath having a lumen with an inner diameter of at least 2 mm and a bending stiffness of approximately 0.08 Nm$^2$, wherein the operative configuration, the elongate body extends through the introducer sheath.

BRIEF DESCRIPTION OF THE DRAWINGS

FIGS. 1A-1G are schematic illustrations of an example arthroscopic drill bit tip. The drawings include the fluted feature, the decreasing flute depth, and a margin.

FIGS. 3A-B are schematic side views of an example assembly with a preset curved inner sheath extended distally from the straight outer cannula with the drill bit extending from the preset curved inner sheath into the joint space.

DETAILED DESCRIPTION

Figure 1A:
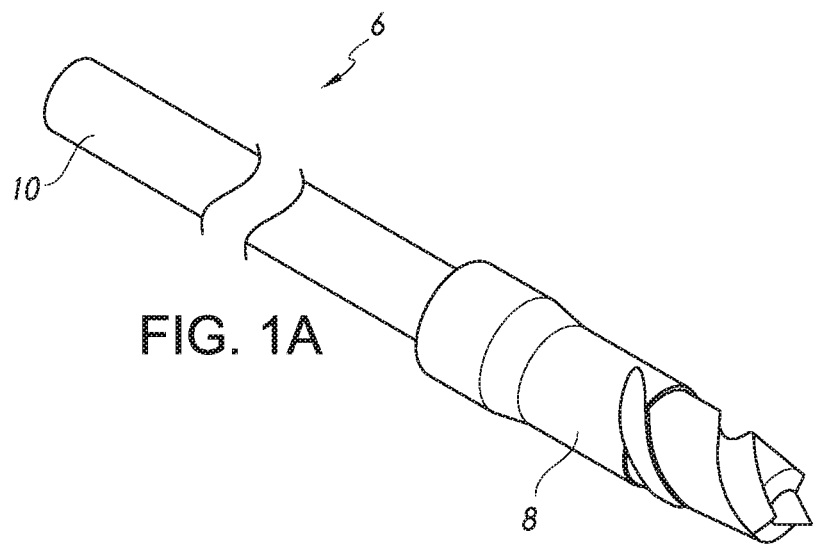

Microfracturing (e.g. a procedure that entails making numerous holes in the bone in the joint space) may lead to increased joint healing albeit with fibrous cartilage, for example after 2 years. Migration of new cartilage may occur as a result. Pervasive drilling through the damaged joint surface may be required (e.g. making sure to drill as many holes as closely spaced as possible in the affected area) and also debriding the old damaged cartilage may be required for cartilage healing to occur reliably. To achieve this end using the current handpiece drilling and cutting blades and burrs is challenging and time consuming for the surgeon. Due to mechanical limitations of currently available designs, the blades must be large to remain robust and, as a result, cannot access the joint pervasively. Additionally, there are simply times when a straight drill blade may not access the affected area completely. Because a fluted drill bit design may be significantly more efficacious than a burr or rotating sharpened edge for drilling applications, a fluted drill design may be desirable for these applications requiring significant drilling. However, the weaker nature of standard fluted drill design at the proximal base of the flutes may make it problematic to utilize for general drilling and shaving purposes (perhaps much less in steerable applications). However, adaptations of a fluted drill design may be desirable, such as a design that can withstand the lateral forces being exerted on the blade bit during drilling and can additionally allow for effective shaving and debridement from a single high-speed drill blade.

Situations also may arise where surgeons may need to perform several procedures within the same location in the joint space. Various access cannulas exist for such purposes, however, most devices of this type require that the drill blade system would have to be removed for further access even though this may result in loss of the specific area of interest. A desirable device for such situations as these may allow for very specific steerable access in constrained joint spaces and may provide a useful (and targeted) access cannula to the affected area by, for example, disconnecting from the driver handpiece and removing the inner cutting blade.

Examples described herein relate generally to interchangeable blade systems for arthroscopic drilling. Examples of arthroscopic suction drilling and shaving systems are described and, in some embodiments, steerable drilling and shaving systems are described combining an arthroscopic drill blade with optional suction drilling for access to the joint space without utilization of open surgical procedures.

In some example systems, the suction drill is purposefully designed to drill a multitude of holes through cartilage and bone in the joint space providing multiple anchor points for bone and cartilage adhesion during regrowth. Potential applications include not only arthroscopic drilling, but also in some embodiments steerable drilling and shaving systems for the drilling of hard to reach areas of the human joint and additionally for biopsy of the bone or cartilage in the joint space. In some example systems, the suction drill is also purposefully designed to function as a side shaver for debriding damaged (or ingrown) cartilage and bone.

It is to be understood that this disclosure is not limited to the particular structures, process steps, or materials disclosed herein, but is extended to equivalents thereof as would be recognized by those ordinarily skilled in the relevant arts. It should also be understood that terminology employed herein is used for the purpose of describing particular embodiments only and is not intended to be limiting. Alterations and further modifications of the inventive features illustrated herein, and additional applications of the principles of the inventions as illustrated herein, which would occur to one skilled in the relevant art and having possession of this disclosure, are to be considered within the scope of the disclosure. Moreover, advantages of example systems and disadvantages of conventional systems are described herein to facilitate an appreciation of the described systems and methods. It is to be understood that not all example systems may have all, or even any, of the described advantages or solve all, or even any, of the described disadvantages.

Example arthroscopic drill systems are provided for general arthroscopic drilling and shaving, and in some examples as a steerable bone and cartilage drilling and shaving system for accessing difficult to reach joint spaces for better coverage microfracture procedures or cartilage biopsies using a steerable drilling and shaving system. Example arthroscopic drill systems combine a rotational/alternating driver source, such as Stryker Formula Shaver handpiece or Smith & Nephew DYONICS POWERMAX ELITE handpiece, with suction supplied to the cutting blades and rotation actuation controlled by the driver (and/or the handpiece or footswitch). In some examples, an arthroscopic drill system may be in the form of an access system, which can function as a guide cannula to perform biopsy or further revision after the drill blade is removed from the path created in the joint space or in the bone using the drill cutting blade. In some examples, the blade design may allow for side cutting by the blade without preventing and/or reducing an obstruction of the ability to cut cores from the bone surface or cartilage using the tip of the blade. In some examples, the blade design may incorporate a diminishing flute geometry resulting in the blades drill flute decreasing along some portion of its length.

Example side cutting blades may be characterized by a drill bit which functions to partially and/or completely clear material as it is advanced forward or as it is swept from side to side or applied laterally against a bone or cartilage surface. This functionality may be facilitated by incorporating a margin (e.g. a 0.127 mm-0.381 mm (0.005 in-0.015 in) margin) and a clearance (e.g. 0.063 mm-0.254 mm (a 0.0025 in-0.010 in) body clearance) on the leading edge and diameter surface of the flute geometry along the drill towards the base of the cutting surface. Examples may be incorporated in whole or in part on the length or some partial length of the blade's drill flute. To further increase the debriding capabilities of some examples one or more wipers and/or one or more cutting guards may extend toward the tip to allow the side cutting feature to shear the material being removed against the guard which acts as a shear point. The wiper/cutting guard may terminate back from the blade tip so as to reduce and/or eliminate any negative impact on the drilling/coring functionality.

Examples of diminishing flute geometry may be characterized by a gradual reduction in the flute depth in relation to the greater drill diameter along the length of the blade bit. Examples may be incorporated in whole or in part on the length or some partial length of the blade's drill flute. Examples may facilitate increased strength along the length of the drill bit as forces applied increase along the length of the blade drill bit proximally toward the driver system. (e.g. forces applied at the tip may have the greatest moment arm applied against the thinnest part of the drill cross-sectional profile the farther from the tip that opposite forces are applied. Reduction of the flute depth in relation to the greater drill diameter generally increases the cross-sectional area profile to increase the drill bit strength.) During the performance of typical microfracturing or biopsy procedures the surgeon must often exert forces at an angle or advance the blade at an angle to the surface being penetrated causing lateral force-loading on the blade drill tip. Examples described herein may be designed to reduce the incidence of blade breakage during these procedures.

Steerable or curved examples may be characterized by an internal flexible drill bit which functions to transmit the rotational energy imparted by the driver system to the drill/blade tip within a flexible outer sheath, preset curved outer cannula/sheath, and/or shape-set curved intermediary cannula which advances in a curved trajectory by deploying from a straight outer sheath attached to the driver system. For that purpose, the steerable drilling and shaving blade may have a combination of features. The rotating inner-shaft element may be composed of a tight, spiral-wound shaft which can transmit rotation and some compressive loading. In some examples, the rotating inner-shaft element may be composed of a flexible shaft (which could additionally or alternately be composed of a laser-cut tube or rod) to transmit rotation and compressive loading. Further, the outer sheath encompassing the inner rotating element may be constructed of a preformed cannula which is bent to an optimal angle of curvature. Thus example preformed cannulas may be positioned to access difficult inter-cavity locations which may not be accessed by direct positioning with a straight cannula. Additionally, example preformed cannulas may be constructed of a material with appropriate modulus of elasticity (such as nitinol, CoCr, and/or PEEK) such that if bent straight, the preformed cannula may spring back to the predetermined curvature when straightening forces were reduced and/or removed. If used in conjunction with an additional straight outer sheath, the straight outer sheath cannula may be advanced into the cavity space and the preformed curved cannula may be advanced from the distal end of the straight cannula to create an adjustable curvature (e.g. depending on the length of curvature still confined within the straight cannula) extending beyond the distal tip of the straight portion. With the curvature at the desired variable angle and the tip optimally positioned for the desired access, the internal flexible drill shaft may be extended to drill or debride the desired hole or area. Advancing and retracting as well as rotating the preformed curved sheath/cannula may allow for improved positioning ability for the alignment/access at the tip in a sphere radiating out from the distal tip of the outer straight cannula. If the inner flexible drill shaft was completely retracted while leaving the outer straight and intermediate preformed cannulas in place, the cannulas may act as an access cannula for delivery or removal of other materials (e.g. such as bone cement or stem cells) or surgical tools (e.g. biopsy).

In some examples of the steerable blade drill and access, the blade may include an inner flexible drill shaft as described herein; however, it may be confined within an actively steerable outer sheath/cannula. In some examples, the outer steerable sheath may be constructed of a (typically) laser-cut cannula with patterns (e.g. chevron patterns) along the length. Depending on the orientation and thickness of the patterns, differing flexibilities and curvature capabilities may be provided. Wires and/or ribbons may be soldered within the laser-cut cannula can act to exert force upon one side of the cannula while releasing tension on the opposite side to create a shorter radius on the tensioned side and curve the cannula in that direction. Using a control handle, examples may allow for steering ability for the alignment/access during drilling/shaving in the joint cavity.

Figure 1B:
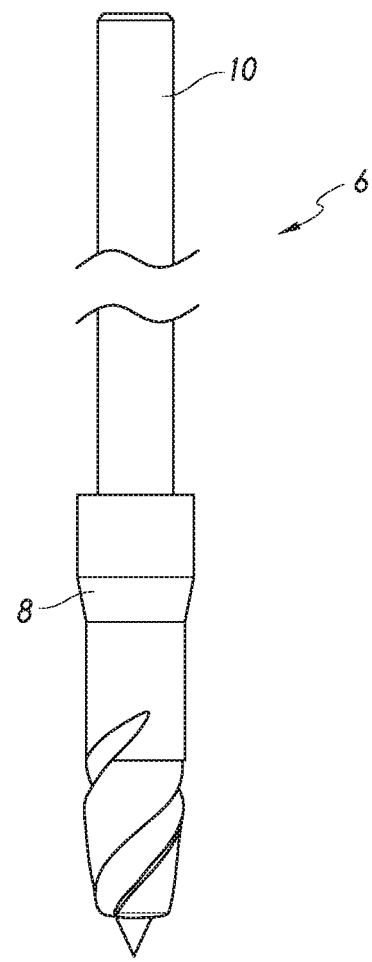

FIG. 1A shows an isometric view of an arthroscopic drill 6 with a drill bit 8 and a body 10. FIG. 1B shows a side view of the arthroscopic drill 6 of FIG. 1A, with a drill bit 8 and a body 10. In an example, a portion of the body 10 may be made from specialized stainless steel, Nitinol, copper, aluminum, titanium, or combinations thereof. In an example, a critical temperature of the Nitinol is selected to be less than a temperature in an operative environment for the drill and wherein a desired shape for the drill is memorized for temperatures above the critical temperature so that the desired shape of the drill 6 may be restored after use. In an example, the drill bit 8 may be secured to the body 10 using welding or other secure attachment methods.

FIG. 1C shows an enlarged view of the drill bit 8 of FIG. 1B with a land area 102, a flute area 104, a lip relief angle 106, a lip angle 110, a land width 112, a helix 114, an external flute tapered angle 115, a point angle 116, a step up area 108, a diameter 118, a body length 120, a flute length 122, an overall length 124, a shank 126, a tapered neck 128.

In an example, the external flute tapered angle 115 may be within a range of angles of about 13 to about 17 about degrees. In an example, the step up area 108 may be used to center the drill bit 8 as it engages with a material during operation.

Figure 1E:
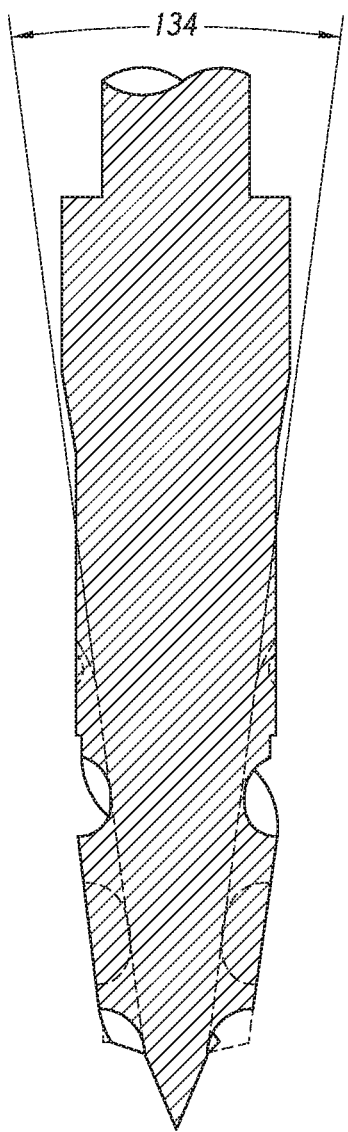

FIG. 1D shows a bottom view of the drill bit 8 of FIG. 1C with a single margin 502. The drill bit 508 may have a web 532, a lip 510, a land width 512, a clearance diameter 513, a body diameter clearance 515, a margin 517, a chiseled edge angle 520, a chisel 522. In an example, the margin 517 may be in the range of 0.127 mm-0.381 mm (0.005 in-0.015 in). In an example, the body clearance diameter 515 may be 0.063 mm-0.254 mm (0.0025 in-0.010 in). In an example, the drill bit 508 may have flutes which reduce in depth so that the flutes disappear over a defined length of the drill bit 508 tip resulting in a thickening of the minor diameter of the drill bit tip progressing toward the proximal base of the drill bit tip, as shown in FIG. 1E. In an example, the drill bit 508 tip margin 517 and body clearance 515 are incorporated in whole or in part on the length or some partial length of the blade's drill flute.

FIG. 1E shows a cross-sectional view of the drill bit 8 of FIG. 1C along line 1E-1E with a diminishing flute angle 134. In an example, the diminishing flute angle 134 may be within the range of angles of about 14 degrees to about 18 degrees.

Figure 1F:
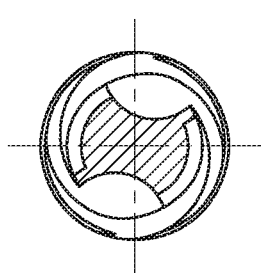

FIG. 1F shows a cross-sectional view of the drill bit 8 of FIG. 1C along line 1F-1F.

Figure 1G:
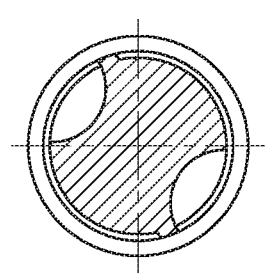

FIG. 1G shows a cross-sectional view of the drill bit 8 of FIG. 1C along line 1G-1G.

Figure 2A:
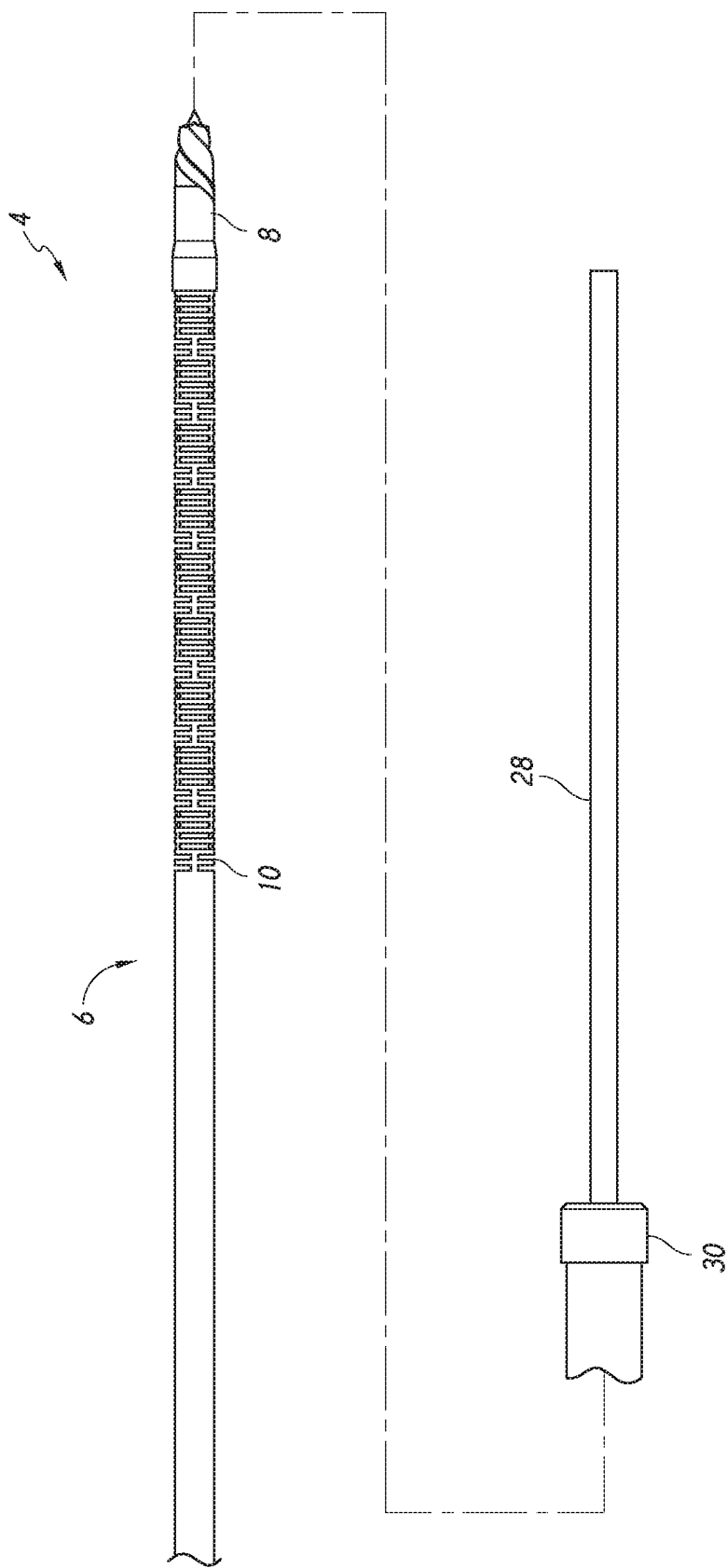
FIGS. 2A-2B are exploded schematic side views of an example assembly.

FIG. 2A shows an exploded view of an assembly 4 of an arthroscopic drill 6 for insertion into a human joint with a drill bit 8 connected to a body 10 which may fit inside an outer sheath 28 with a handle 30. In an example the outer sheath 28 may be a hollow tube with a thickness between 0.025 mm and 0.203 mm (0.001 in and 0.008 in). In an example, the outer sheath 28 lumen may have an inner diameter of at least 2 mm (0.078 in) and a bending stiffness of approximately 0.08 Nm2. In an example, the body 10 may have a first portion formed as a solid mass of a material different from a material of which a second portion. The second portion may be formed with an outer diameter smaller than that of the first portion. In an example, the body 10 may have a first portion is formed as a solid mass of a material different from a material of which the second portion is formed, the second portion including cut-outs reducing a bending stiffness thereof. In an example, the body 10 may have a first or second portion formed of stainless steel. In an example, the body 10 may have a first portion or a second portion formed of a material with an elastic modulus E ranging from between 482,633 Bar-689,475 Bar (7,000,000 psi to 10,000,000 psi).

In an example, the sheath 28 protecting the rotating arthroscopic drill 6 may be formed of nitinol, cobalt chromium, or PEEK.

In an example, a tissue receiving opening is formed laterally through a wall of the distal portion of the outer sheath 28.

Figure 2B:
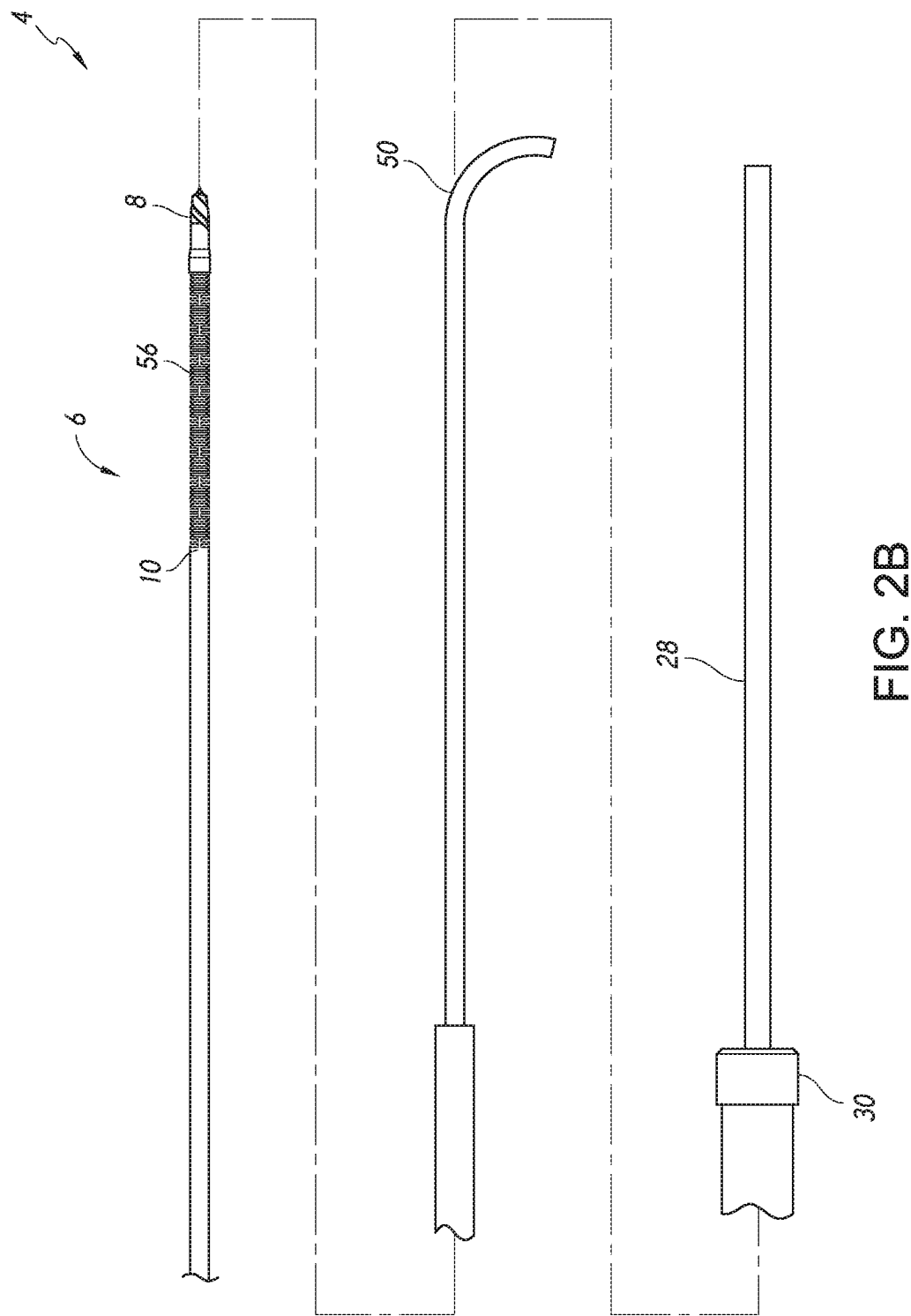

FIG. 2B shows an exploded view of an example assembly 4 of an arthroscopic drill 6 for insertion into a human joint a drill bit 8 connected to a body 10 which may fit inside a preset curved inner sheath 50 which may tit inside an outer sheath 28 with a handle 30. In an example, the preset curved inner sheath 50 may be formed such that it can be straightened by straightening forces when inserted into the outer sheath 28, but it springs back to the preformed curve when the straightening forces are released and a distal portion of the preset curved inner sheath 50 extends from a distal portion of the outer sheath 28. In an example, the preset curved inner sheath 50 may be formed of nitinol, cobalt chromium, or PEEK, or other materials.

In an example, the preset curved inner sheath 50 is introduced into the joint space of the joint 300 (see FIGS. 3A and 3B) within a straight outer sheath 28 which serves to constrain and straighten the preset curved inner sheath 50 while being placed, but which allows the preset curved inner sheath 50 to extend distally beyond the outer sheath 28 and assume some portion or the whole curvature of the preformed curve based upon how much of the preset curved inner sheath 50 is extended out of the outer sheath 28.

In an example, the preset curved inner sheath 50 is laser cut with chevrons or slots to increase its flexibility. In an example, the preset curved inner sheath 50 may be constructed with internal tensioning ribbon or wire elements to pull on the tip of the preset curved inner sheath 50 to cause the preset curved inner sheath 50 to steer towards the direction of the tensioning element with a reduced length due to a steering handle which tensions or releases the tensioning elements under user guidance. The tensioning elements would be adjacent an outer surface of the preset curved inner sheath 50 but still be installed within the outer sheath 28 when deploying into a human joint.

FIG. 3A shows an example assembly 4 of an arthroscopic drill 6 inserted into a joint 300, with a handle 30 and an introducer sheath 28 housing the majority of the body 10 (not shown), and a distal portion of the preset curved inner sheath 50 extending from a distal portion of the outer sheath 28. In this example, the preset curved inner sheath 50 is slightly extended from the distal end of the outer sheath 28 such that the drill bit 8 extends from the preset curved inner sheath 50 at an approximate 45-60 degree angle from the central axis of the outer sheath 28. The length of the preset curved inner sheath 50 that extends from the outer sheath 28 dictates the angle of the drill bit 8. In an example, the body 20 may have a deflection portion 56 connected to the tip 8. The deflection portion 56 has cut out features to increase the flexibility of the body 10. In this example, a suction force may be applied through the outer sheath to surround the drill 6.

FIG. 3B shows an example of an assembly 4 of an arthroscopic drill 6 inserted into a joint, with a handle 30 and an introducer sheath 28 housing the majority of the body 10 (not shown) and a distal portion of preset curved inner sheath 50 extending from a distal portion of the outer sheath 28. In this example, the preset curved inner sheath 50 is further extended from the distal end of the outer sheath 28 than in FIG. 3A, such that the drill bit 8 extends from the preset curved inner sheath 50 at an approximate 80-90 degree angle from a central axis of the outer sheath 28. The length of the preset curved inner sheath 50 that extends from the outer sheath 28 dictates the angle of the drill bit 8. In this example, since more of the distal portion of the preset curved inner sheath 50 is extended from the outer sheath 28, the drill bit makes a sharper angle compared to the central axis of the outer sheath 28. In an example, the body 10 may have a deflection portion 56 connected to the tip 8. The deflection portion 56 has cut out features to increase the flexibility of the body 10. In this example, a suction force may be applied through the preset curved inner sheath 50 surrounding the drill 6.

In an example, the joint is a human joint, and the assembly 4 is placed adjacent the surface of the human joint. In an example, a tissue receiving opening is formed laterally through a wall of the distal portion of the preset curved inner sheath 50.

Figure 4A:
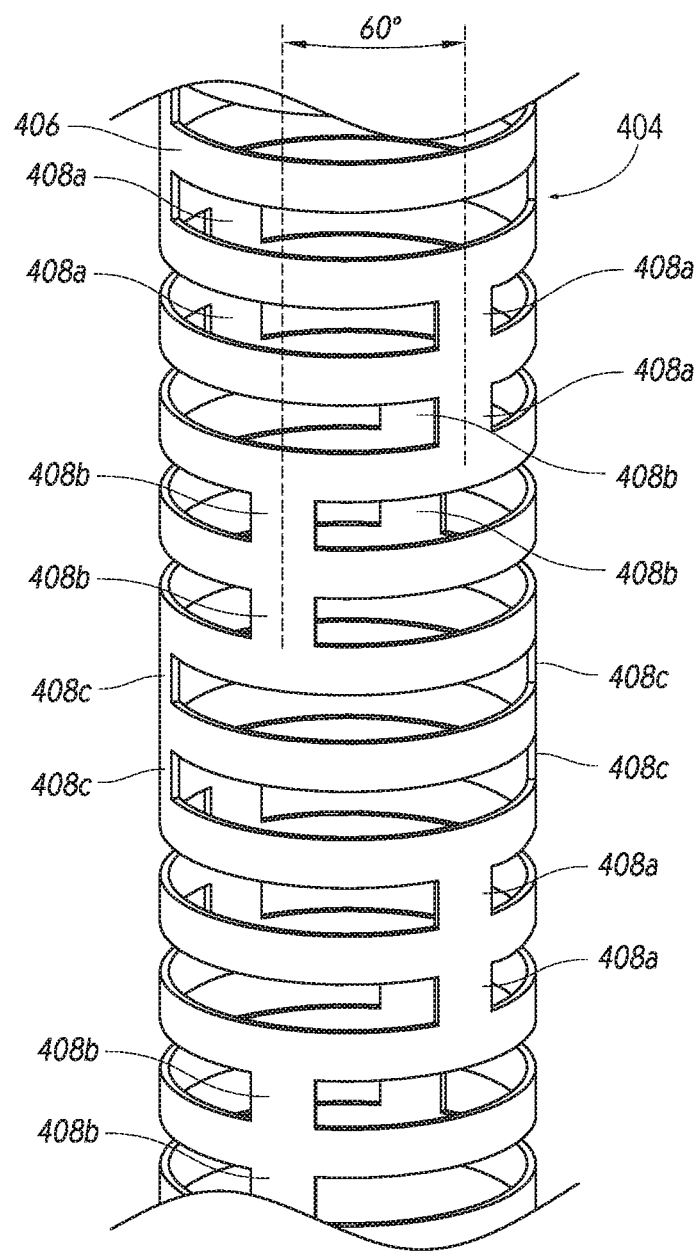
FIGS. 4A-4C are schematic illustrations of a deflection portion of an arthroscopic drill bit.

FIG. 4A shows an example of a deflection portion 56 of a body 10 of an arthroscopic drill 6. In this example, the deflection portion 56 may have multiple sections 404 formed through a material removal process, such as laser cutting. The deflection portion 56 may have rings 406 with a set of connector links 408 that are 180 degrees opposite of each other connecting the rings 406. In an example, a set of two connector links 408a may be positioned 60 degrees offset from a set of two connector links 408b which are positioned 60 degrees offset from a set of two connector links 408c. In an example, the pairs of connector links 408 spiral along the length of the deflection portion 56 in order to create a helix of the rings 406 spiraling along the arthroscopic drill 6 to increase the flexibility of the arthroscopic drill 6 as it is rotated.

In an example, a similar pattern of rings and connector links may be used on the preset curved inner sheath 50 to increase its flexibility when assembled and moved within the outer sheath 28.

Figure 4B:
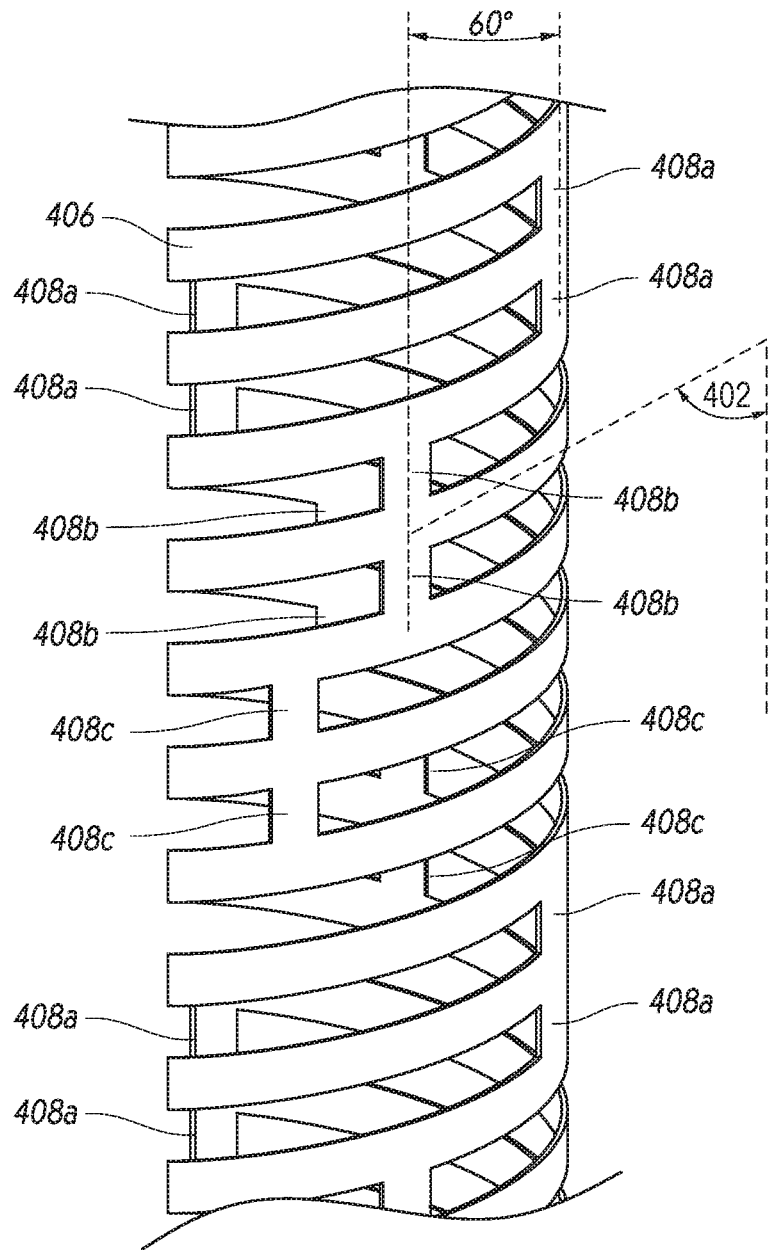

FIG. 4B shows an example of a deflection portion 56 of a body 10 of an arthroscopic drill 6, similar to that of FIG. 4A, but the rings 406 may be formed at an angle 402 from the central axis of the deflection portion 56. In an example, the angle range may be between 45 and 60 degrees. In an example, angle 402 may be incorporated due to the clockwise rotation of the drill shaft during operation. In an example, the angled rings of FIG. 4B may be used on the deflection portion 56 of the body 10 when the preset curved inner sheath 50 is also laser cut. The use the angled rings may prevent the drill 6 from binding inside the preset curved inner sheath 50 when the drill 6 is rotating.

In an example, a similar pattern of rings and connector links may be used on the preset curved inner sheath 50 to increase its flexibility when assembled and moved within the outer sheath 28.

Figure 4C:
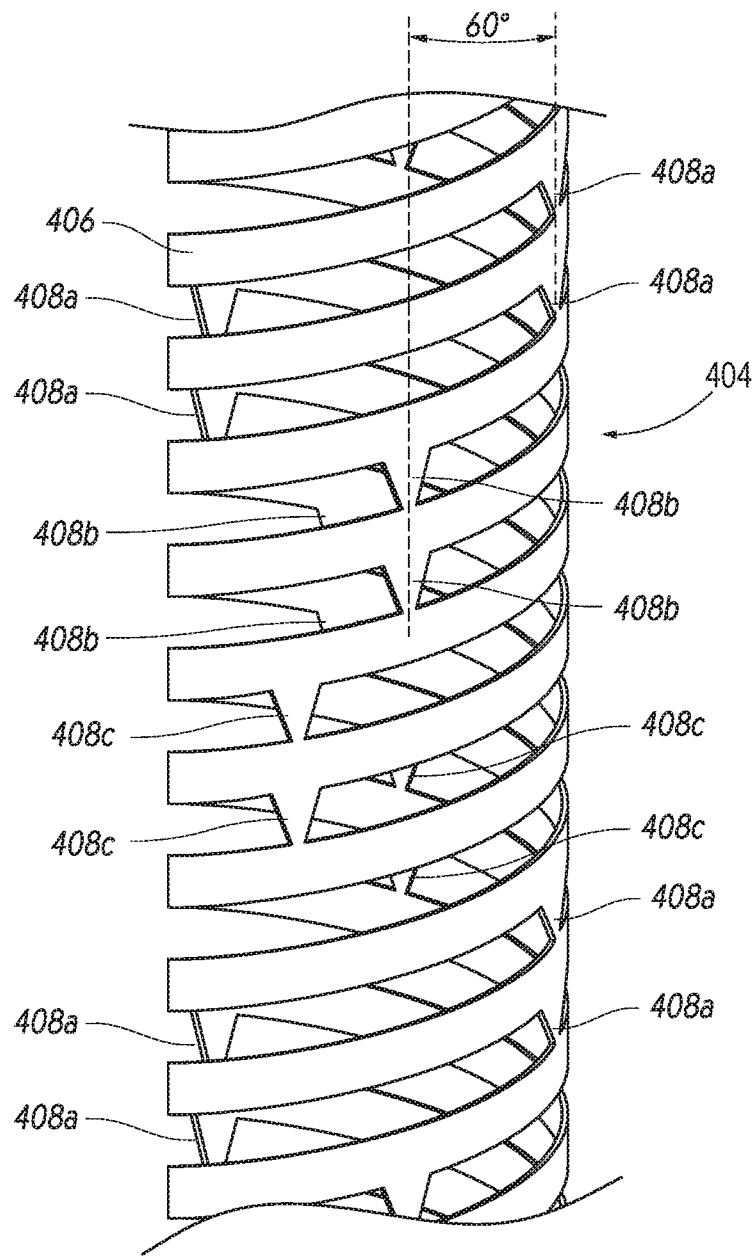

FIG. 4C shows an example of a deflection portion 56 of a body 10 of an arthroscopic drill 6. In this example, the deflection portion 56 may have multiple sections 404 formed through a material removal process, such as laser cutting. The deflection portion 56 may have rings 406 connected by chevron shapes 410 or other shapes cut 180 degrees opposite each other. In an example, the rings 406 and chevrons 410 may be formed at an angle 402 from the central axis of the deflection portion 56. In an example, the angle 402 may range between 45 and 60 degrees. In an example, a set of two connector chevrons 410a may be positioned 60 degrees offset from a set of two connector links 410b which are positioned 60 degrees offset from a set of two connector links 410c.

In an example, a similar pattern of rings and connector links may be used on the preset curved inner sheath 50 to increase its flexibility when assembled and moved within the outer sheath 28.

Figure 5A:
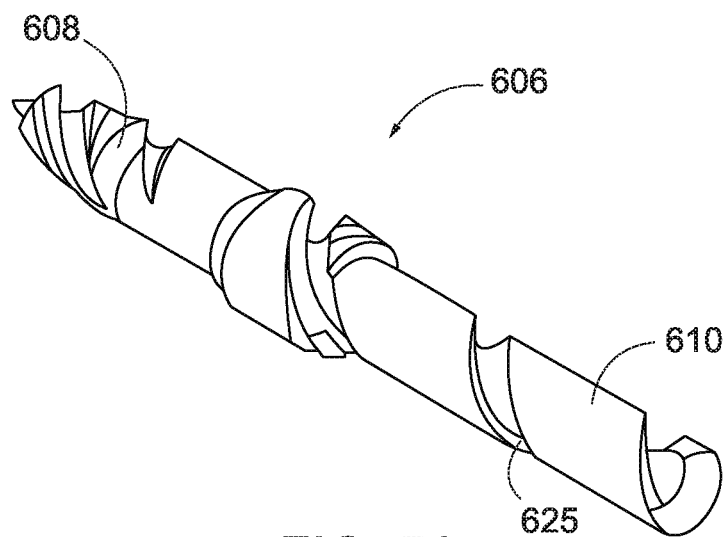
FIGS. 5A-5C are schematic illustrations of an example arthroscopic drill bit tip. The drawings include the fluted feature, the decreasing flute depth, and a margin.
Figure 5B:
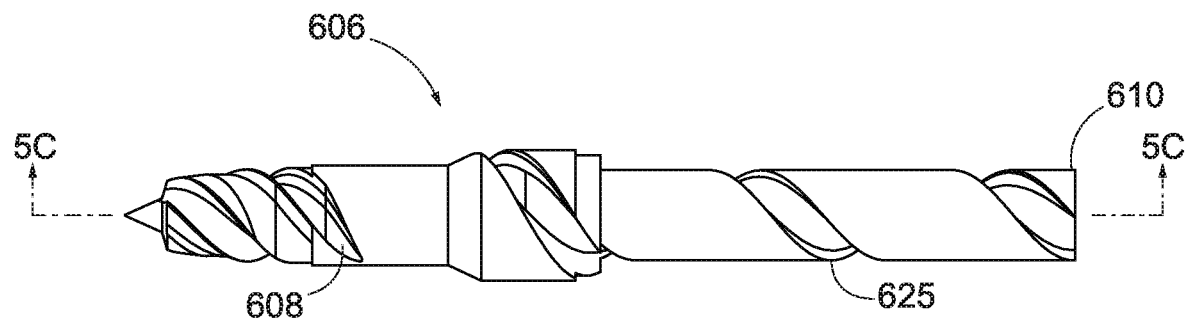
Figure 5C:
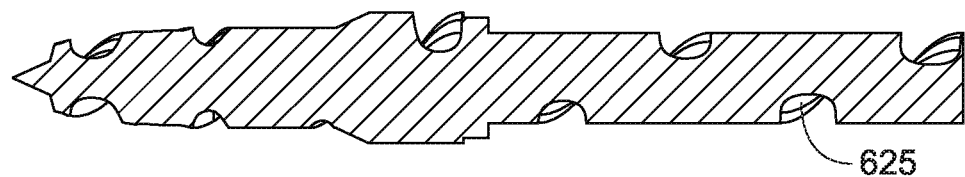

FIGS. 5A-5C are schematic illustrations of an example arthroscopic drill bit tip. The drawings include the fluted feature, the decreasing flute depth, and a margin. FIG. 5A shows an isometric view of an arthroscopic drill 606 with a drill bit 608 and an elongate body 610. FIG. 5B shows a side view of the arthroscopic drill 606 of FIG. 1A, with a drill bit 608 and a body 610. FIG. 5C shows a cross-sectional view of the drill bit 608 of FIG. 5B along line 5C-5C.

The arthroscopic drill 606 of FIG. 5A-5C may be similar to the arthroscopic drill 6 of FIGS. 1A-3B. The arthroscopic drill 606 may also include spiraling channel 625 that extends from the drill bit 608 and through the body 610. The spiraling channel 625 may extend from the proximal end of the body 610 to the distal end of the body 610 adjacent drill bit 608. In an example, the drill bit 608 may be welded into the inner rotating cannula of the device.

In an example, the spiraling channel 625 may have a depth and a width. In an example, the width of the spiraling channel 625 may be generally constant. In other examples, the width of the spiraling channel 625 may vary. In an example, the depth of the spiraling channel 625 may be constant. In other examples, the depth of the spiraling channel 625 may vary. In an example, there may be a chamfer on the edge or border of the spiraling channel adjacent an outer surface of the body 610. The spiraling channel 625 may be formed within the body 610 and may extend up the body at an angle between 20 and 60 degrees. In an example, the spiraling channel 625 spirals up the body 610 at a 45 degree angle. As shown in FIG. 5C, the spiraling channel may form an indention in the body 610 with sloped walls and a rounded bottom region. In an example, the spiraling channel 625 may be smooth without sharp corners at the area where the walls connect with the bottom region to help prevent regions or points of weakness.

During operation, the spiraling channel 625 may create a suction pathway or channel for the material being removed by the rotation of the drill bit 608. The spiral nature of the spiraling channel 625 may allow the creation of the suction channel without adding a focal weak spot to the body 610. During operation, the spiraling channel may also provide an auguring or boring effect to help manually draw the material into the tip of the drill bit 608 and the inner cannula while it is rotating.

COMPONENTS

4 assembly

6 arthroscopic drill 8 drill bit
10 body
28 introducer sheath
30 handle
50 preset curved inner sheath
56 deflection portion
102 land area
104 flute area
106 lip relief angle
108 step up area
110 lip angle
112 land width
114 helix
115 external flute tapered angle
116 point angle
118 diameter
120 body length
122 flute length
124 overall length
126 shank
128 tapered neck
134 diminishing helix angle
300 joint
402 angle
404 sections
406 rings
408 connector links
410 chevron
508 drill bit
510 lip
512 land width
513 clearance diameter
515 body clearance diameter
517 margin
520 chiseled edge angle
522 chisel
532 web
606 arthroscopic drill
608 drill bit
610 body
625 spiraling channel

What is claimed is:

1. An assembly of an arthroscopic drill configured for insertion into a human joint of a human body, the assembly comprising:
an elongated body extending between a proximal end which, during use, is configured to remain external to the human body and a distal end which, when in an operative configuration, is configured to be positioned in the human joint adjacent to a target structure within the human body;
a drill bit having a proximal portion connected to the distal end of the elongated body, the drill bit having a distal portion configured to extend to the target structure, wherein the drill bit includes a drill bit tip, and wherein a distal end of the drill bit tip comprises one or more flutes which reduce in depth so that the flutes disappear over a length of the drill tip resulting in a thickening of a minor diameter of the drill bit tip progressing toward a proximal end of the drill bit; and
at least one sheath having a lumen, wherein in the operative configuration, the elongate body extends through the lumen of the at least one sheath.

2. The assembly of claim 1 further comprising a spiraling channel formed in an exterior surface of the elongate body and a portion of the drill bit, wherein the spiraling channel has sloped walls and extends at an angle of between 20 and 60 degrees up the full length of the elongate body to create a suction pathway for material being removed through rotation of the drill bit.

3. The assembly of claim 1, wherein the elongate body includes a distal portion and a proximal portion, a bending stiffness of the proximal portion being less than a bending stiffness of the distal portion and/or of the drill bit.

4. The assembly of claim 3, wherein the second portion comprises a plurality of rings, adjacent ones of the plurality of rings connected by connector links.

5. The assembly of claim 4, wherein each pair of adjacent rings of the plurality of rings is connected by a pair of connector links at diametrically opposite sides of the pair of adjacent rings.

6. The assembly of claim 4, wherein the plurality of rings are angled with respect to a central axis of the second portion.

7. The assembly of claim 1, wherein the one or more flutes are in a fluted portion of the drill bit, which is tapered at an angle between 13 degrees and 17 degrees.

8. The assembly of claim 7, wherein the drill bit comprises a margin of 0.127 mm to 0.381 mm along at least a portion of the one or more flutes.

9. The assembly of claim 1, wherein the at least one sheath includes a curved inner sheath and an outer sheath, wherein the curved inner sheath is configured for insertion into a lumen of the outer sheath whereby the inner sheath bends when inserted through the outer sheath.

10. The arthroscopic drill of claim 9, wherein the curved inner sheath comprises nitinol, cobalt chromium, or PEEK.

11. The arthroscopic drill of claim 1, wherein a distal portion of the elongated body is made from stainless steel, nitinol, copper, aluminum, titanium, or combinations thereof.

12. An arthroscopic drill configured for insertion into a human joint of a human body, the arthroscopic drill comprising:
an elongated body extending between a proximal end which, during use, is configured to remain external to the human body and a distal end which, when in an operative configuration, is configured to be positioned in the human joint adjacent to a target structure within the human body;
a drill bit having a proximal portion adjacent the distal end of the elongated body, the drill bit having a distal portion configured to extend to the target structure;
an outer sheath having a lumen, wherein in the operative configuration, the elongated body extends through the lumen of the outer sheath;
a flexible inner sheath around the drill bit, the flexible inner sheath inserted in the outer sheath; and
a spiraling channel formed in the elongated body and extending to the drill bit to provide a pathway from the drill bit through the elongated body for material being removed from the target structure by rotation of the drill bit.

13. The arthroscopic drill of claim 12, wherein the outer sheath is straight and the inner sheath is preformed with a curve which can be straightened by straightening forces, but which springs back to the preformed curve when the straightening forces are released when the inner sheath is extended out of the outer sheath.

14. The arthroscopic drill of claim 13, wherein the flexible inner sheath comprises nitinol, cobalt chromium, or PEEK.

15. The arthroscopic drill of claim 12, wherein the spiraling channel extends at an angle of 20 to 60 degrees along the elongate body.

16. The arthroscopic drill of claim 15, wherein the spiraling channel extends at an angle of 45 degrees along the elongate body.

17. The arthroscopic drill of claim 15, wherein the spiraling channel comprises an indentation in the elongate body having sloped walls and a rounded bottom region.

18. The arthroscopic drill of claim 12, wherein the spiraling channel extends the full length of the elongate body.

19. An arthroscopic drill configured for insertion into a human joint of a human body, the arthroscopic drill comprising:

an elongated body extending between a proximal end which, during use, is configured to remain external to the human body and a distal end which, when in an operative configuration, is configured to be positioned in the human joint adjacent to a target structure within the human body;

a drill bit having a proximal portion adjacent the distal end of the elongated body, the drill bit having a distal portion configured to extend to the target structure;

an outer sheath having a lumen, wherein in the operative configuration, the elongated body extends through the lumen of the outer sheath; and a flexible inner sheath around the drill bit, the flexible inner sheath inserted in the outer sheath;

wherein the flexible inner sheath is lasercut with chevrons or slots and constructed with internal tensioning elements to pull on a tip of the flexible inner sheath and cause the tip of the flexible inner sheath to steer towards a direction of one of the internal tensioning elements with reduced length due to a steering handle which tensions or releases the internal tensioning elements under user guidance.

20. The arthroscopic drill of claim 19, wherein the outer sheath is straight and the inner sheath is preformed with a curve which can be straightened by straightening forces, but which springs back to the preformed curve when the straightening forces are released when the inner sheath is extended out of the outer sheath.

21. The arthroscopic drill of claim 20, wherein the flexible inner sheath comprises nitinol, cobalt chromium, or PEEK.

* * * * *